United States Patent
Wilner

[11] Patent Number: 6,001,083
[45] Date of Patent: Dec. 14, 1999

[54] SHARPS PROTECTION SYSTEM

[76] Inventor: Mark C. Wilner, 20 Waterside Plz., #32J, New York, N.Y. 10010

[21] Appl. No.: 09/187,600

[22] Filed: Nov. 6, 1998

[51] Int. Cl.[6] .................................................... A61M 5/00
[52] U.S. Cl. ........................................... 604/263; 604/110
[58] Field of Search ................................ 604/110, 192, 604/197, 198, 263, 162, 164, 167

[56] References Cited

U.S. PATENT DOCUMENTS

| | | | |
|---|---|---|---|
| 4,676,783 | 6/1987 | Jagger et al. | 604/171 |
| 4,941,881 | 7/1990 | Masters et al. | 604/162 |
| 5,057,087 | 10/1991 | Harmon | 604/198 |
| 5,088,982 | 2/1992 | Ryan | 604/110 |
| 5,147,319 | 9/1992 | Ishikawa et al. | 604/174 |
| 5,147,327 | 9/1992 | Johnson | 604/198 |
| 5,176,655 | 1/1993 | McCormick | 604/192 |
| 5,330,438 | 7/1994 | Gollobin et al. | 604/177 |
| 5,354,281 | 10/1994 | Chen | 604/177 |
| 5,382,240 | 1/1995 | Lam | 604/177 |
| 5,527,296 | 6/1996 | Kashanchi | 604/263 |
| 5,562,636 | 10/1996 | Utterberg | 604/263 |
| 5,800,400 | 9/1998 | Hogan | 604/171 |

*Primary Examiner*—Wynn Wood Coggins
*Assistant Examiner*—Sharon Finkel
*Attorney, Agent, or Firm*—Aufrichtig Stein & Aufrichtig, P.C.; Peter D. Aufrichtig

[57] ABSTRACT

A sharps protection system for a blood collection set, needle, syringes, other hollow needle invasive instruments and other sharp instruments such as scalpels. This system includes a sharp pointed needle having a tip at a first end and a handle coupled to the needle proximate to the end of the needle opposite to the tip. A protection mechanism is coupled to the handle and the needle for selectively protecting the tip of the needle from undesired physical contact. The protection mechanism is moveable from a first, inactive state to a second, protective state in which at least the tip of the needle is covered by the protection mechanism and protected against inadvertent contact. The sharps protection system is particularly suitable in connection with a butterfly type IV blood collection set.

63 Claims, 6 Drawing Sheets

SHARPS PROTECTION SYSTEM

BACKGROUND OF THE INVENTION

This invention is generally directed to a sharps protection system and, in particular, to a sharps protection system for blood collection sets including those with butterfly IV structures, needles, scalpels and other sharp instruments intended to penetrate a person's skin.

As the knowledge of medical hazards increases and the threat of transmission of disease, through the transmission of bodily fluids and in particular blood, rises, greater care and concern has been allocated to the disposal of needles, syringes, scalpels and other sharp instruments used for either drawing blood, providing injections or otherwise piercing a patient's skin. A primary concern of the medical industry has been the prevention or avoidance of transmission of disease through the reuse of needles, syringes or other sharp implements. This concern has been dealt with, at least in the first world, with a complete reliance on disposable medical products. To assure that no patient receives a needle or syringe which has been infected by a prior user, at least American and most major developed countries' medical procedures have mandated the use of new sharp needles and syringes in all cases with appropriate disposal of used sharp implements (commonly referred to as "sharps"). The sharps problem has been addressed through the use of sharps disposal boxes which are color coded and maintained in doctors' offices, clinics and hospitals in a convenient fashion which facilitates proper disposal of any sharp implements which are to be discarded. Generally, the physician or nurse would use the sharps instrument on a patient and then, immediately following completion of that use, place the sharps instrument, or at least the sharp component of it, into the sharps collection box. Generally, the sharps collection boxes are configured as plastic containers with a small one-way opening at the top which allows a sharp item to be placed into the container but which prevents a sharp item within the container from being inadvertently removed from the container or falling out. Likewise, the sharps container traditionally has an opening which inhibits the ability of a user to inadvertently place their hand inside the box and touch the sharp items inside the sharps collection box.

While this approach has functioned satisfactorily in connection with most sharps instruments, such as the small razor sharp instruments used to extract a drop or two of blood and needles which are suited for easy disposal, there are other types of sharps instruments which are not adequately dealt with by the current technology.

In particular, a blood collection set including a butterfly IV is commonly used for collection of blood for testing purposes. Generally, the device includes a slender, hollow needle attached to a rubber or plastic or tube, terminating in a connector assembly for connecting to the receptacle for receiving the blood, and a thin, flexible plastic guide in the shape of a butterfly with two wings, one on each side of the needle, which allow the medical professional to slide the flexible needle at a shallow angle to the patient's arm. The butterfly plastic wings aid in the careful placement and guidance of the needle into the patient's arm in a relatively painless and efficient fashion. Once the blood has been drawn from the patient it is then necessary to dispose of the sharp instrument. Because of the tubing and butterfly wings attached to the needle it is often relatively complicated and dangerous to dispose of the set into a sharps container.

Because of the presence of blood on the collection set there is great concern about a medical professional inadvertently pricking his or her finger with the extremely sharp tip of the needle in further handling and in attempting to place the collection set into the sharps container. The same problem exists for other medical instruments, including sharp points and additional components which make handling and insertion of the instrument into the sharps collection box dangerous. Accordingly, there is a need for an improved IV blood collection set and other sharp instruments to be protected so that they may be handled following their use and prior to storage in a sharps container in a fashion which reduces or prevents the risk of the medical professional poking himself or herself with the sharp end of the instrument.

SUMMARY OF THE INVENTION

The invention is generally directed to a sharps protection system for a blood collection set and other sharp instruments. It includes a sharp pointed needle having a tip at a first end. A handle is coupled to the needle, proximate to the end of the needle opposite to the tip. A protection mechanism, coupled to the handle end of the needle selectively protects the tip of the needle from undesired physical contact. The protection mechanism is moveable from a first, inactive state to a second, protective state in which at least the tip of the needle is covered by the protection mechanism and protected against inadvertent contact.

Accordingly, it is an object of the invention to provide an improved sharps protection system in which the sharp end of a medical instrument is covered and inadvertent contact between the sharp implement and a user's body is prevented.

Still another object of the invention is to provide an improved sharps protection system for a butterfly style blood collection set which is integrally formed with the medical instrument.

A further object of the invention is to provide an improved sharps protection system in which the sharp tip of the medical instrument is unaffected in its traditional usage but which is covered through an integrally formed sharps protection system built into the medical instrument which may be implemented in a safe fashion following completion of the use of the medical instrument.

Still a further object of the invention is to provide an improved sharps protection system in which a guard member slides along the length of a needle or other pointed implement and locks in position over the tip of the sharp object.

Yet still another object of the invention is to provide an improved butterfly collection set in which a flexible hollow needle and thereafter can be removed from the patient's arm or other limb and capped at the same time so that the risk of the needle point contacting either the medical professional or other user prior to safe disposal of the medical instrument into a sharps container is indicated.

Still yet a further object of the invention is to provide an improved sharps protection system which protects a medical professional or other user from inadvertent contact with the sharp end of the medical instrument prior to disposal.

Still other objects and advantages of the invention will, in part, be obvious and will, in part, be apparent from the specification.

The invention accordingly comprises the features of construction, combinations of elements and arrangements of parts which will be exemplified in the constructions hereinafter set forth, and the scope of the invention will be indicated in the claims.

BRIEF DESCRIPTION OF THE DRAWINGS

For a fuller understanding of the invention, reference is had to the following descriptions taken in connection with the accompanying drawings, in which.

DETAILED DESCRIPTION OF THE PREFERRED EMBODIMENTS

Figure 1:
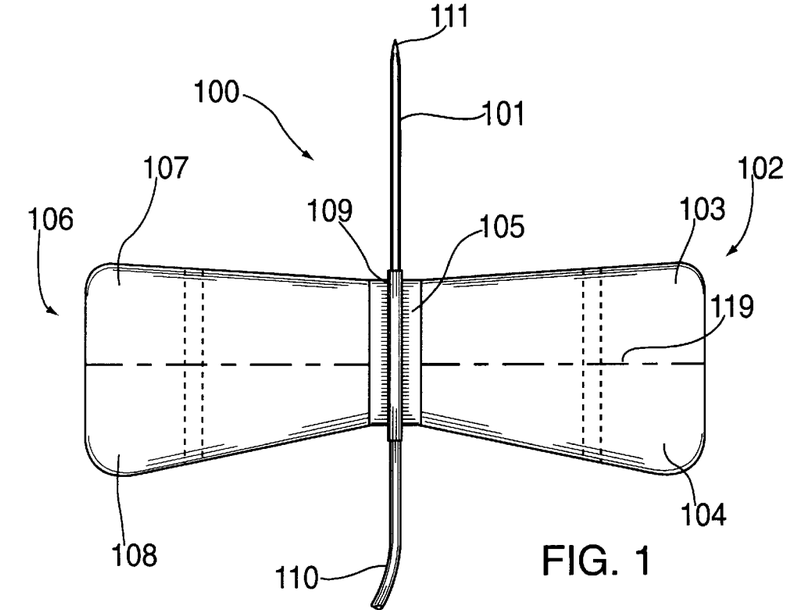
FIG. 1 is a top elevational view of a sharps protection system for a blood collection set constructed in accordance with a first preferred embodiment of the invention.
Figure 2:
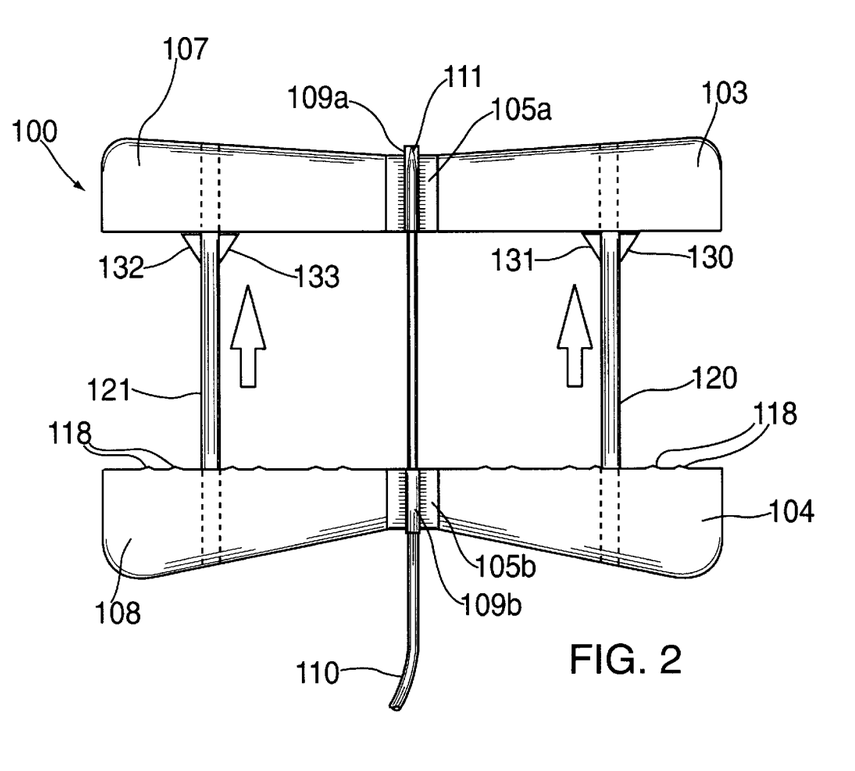
FIG. 2 is a top plan view of the sharps protection system for the blood collection set of FIG. 1 in its post-use sharps protection position.

Reference is first made to FIGS. 1 and 2, wherein a sharps protection system for a blood collection set constructed in accordance with a preferred embodiment of the invention, generally referred to as 100, is shown. Blood collection set 100 is a butterfly IV set commonly used for obtaining blood samples. Blood collection set 100 includes a hollow needle 101 with a sharp tip 111 secured to a tube 110 through which the blood will flow. In preferred embodiments of the blood collection set 100 a connector of a conventional sort (not shown) attaches to the bottom of tube 110 in FIGS. 1 and 2. The blood collection set 100 also includes a butterfly member having wings 102 and 106 which are generally made of a flexible plastic material which allows the tip of needle 111 to be inserted at a shallow angle in accordance with preferred medical techniques.

Generally, once the blood has been collected, the medical professional removes the tip of needle 111 from the patient's arm or other body part and must then safely dispose of the blood collection set in a sharps container. The sharps containers are generally boxes with narrow openings into which needles and other sharp disposable implements are placed for safe handling and disposal. However, because of the needle 101, butterfly wings 102 and 106 and the tubing 110 and connector connected to the needle 101, blood collection set 100 forms an awkward item for disposal. The tip of needle 111 is extremely sharp so as to penetrate the patient's skin and blood vessels with minimal pain. However, this sharpness also heightens the risk of a medical professional coming in contact with the sharp tip and infecting himself or herself with a patient's infectious agent. Particularly because of the size and awkwardness of the blood collection set components the medical professional must generally push the blood collection set through the small opening in the sharps container with his or her fingertips in a series of small steps. This increases the possibility of the medical professional jabbing himself or herself with either the sharp point 111 of the needle 101 or some other sharp instrument inside the sharps collection container.

The sharps protection system for the blood collection set 100 constructed in accordance with preferred embodiments of the invention includes features which reduce or eliminate the risk of inadvertently jabbing oneself with tip 111 of needle 101. Prior to use a sheath (not shown) is present on the needle when the blood collection set is removed from its sterile package. This is removed by sliding the clear plastic sheath off the needle. Following use, it is far too dangerous and risky to attempt to reattach the sheath and good medical procedures forbid such activity.

Butterfly wings 102 and 106 are formed so as to separate along dotted line 119 which represents the perforation of the plastic material forming the butterfly wings 102 and 106. Butterfly wing 102 divides in to upper section 103 and lower section 104 while wing 106 splits into upper section 107 and lower section 108. Needle 101 is connected to tubing 110 and is surrounded by a sheath 109 and support member 105 which couples the wings 102 and 106 together. Sheath 109 protects the connection between needle 101 and tubing 110. As upper sections 103, 107 are moved upward, tabs 130, 131, 132, 133 are exposed and lock in place against the bottom surface of upper sections 103, 107, preventing the upper sections 103, 107 from sliding backward and exposing needle top 111. The tabs 130–133 may also be used against lower wing portions 104, 108 or in both places to affirmatively lock in place. In a preferred embodiment, wings 130–133 make clicking or other sounds as they deploy, providing a positive feedback signal to the health care professional that the needle tip 111 is safely covered. A visual signal, such as a bright color to tabs can also be used to provide positive feedback to the health care professional. In addition, while FIG. 1 is shown with transport arms 120, 121 integral with (or enclosed within) wings 102, 106, they may extend downwardly below the bottom surface of wings 102, 106, depending on the relative weight of the butterfly sections 102, 106 and needle 101. Alternatively, transport arms 120, 121 may be designed as telescoping rods, like an antenna, which can expand several times their closed length. When the collection set is ready for use the medical professional carefully removes and disposes of the plastic sheath. It is strictly against policy to reuse the sheath as the risk of accidental contact with the tip of the needle is too great. Support member 105 couples wings 102 and 106 together and to the needle. When perforation 119 is broken as the upper section of the butterfly wings 102 and 106 move upward, as shown in FIG. 2, sections 103 and 107 carry upper sheath section 109a and upper connector sector 105a along transport arms 120, 121 so that sheath 109a covers tip 111 of needle 101, thereby preventing accidental contact with the sharp tip 111.

In the embodiments of FIGS. 1 and 2 the upper section of the butterfly attachment including wing portions 103 and 107, connector 105a and sheath 109a lock in position so that tip 111 of needle 101 is protected. Transport arms 120 and 121 are configured so as to lock in the position shown in FIG. 2 when extended. In this way tip 111 is covered and handling of the blood collection set in preparation for and during insertion of the blood collection set into the sharps collection container is maintained. Nubs 118 shown in FIG. 2 are the residue of the perforation 119.

In practice, the blood collection set would be used exactly as the current blood collection set is utilized with all functional aspects of the equipment unchanged to the medical practitioner. However, when the practitioner is ready to remove the needle from the patient's arm or other body part, the perforation 119 is separated and, as the back portion including wings 104, 108 are pulled backward out of the patient's arm or other body part, the front portion including wings 103 and 107 are pushed forward so that tip 111 of the needle is not exposed at any point. As it finally is removed from the patient's arm or other body part, it is captured within and protected by the end of sheath 109a. Sheath 109a is shown in FIG. 2 as merely covering tip 111 with very little clearance. In other preferred embodiments, sheath 109a may extend a greater distance beyond tip 111 so as to further prevent inadvertent contact with tip 111. Thereafter, with blood collection set 100 in the position shown in FIG. 2, the entire set is then placed in the sharps collection container.

The transport arms 120, 121 are shown by way of example. Alternative approaches in which an extension and separation of the two portions of the butterfly wing 102, 106 is short, while locking the protective sheath 109a around needle tip 111 may be utilized. In practice, it is important that the transport arms 120, 121 lock the sharps protection system for the blood collection set in the position shown in FIG. 2 and that the upper portions of the butterfly wings, 103, 107 not either slide off or move downward in the direction opposite to that of the arrow shown in FIG. 2. Various conventional locking mechanisms may be incorporated in the sharps protection system.

Figure 3:
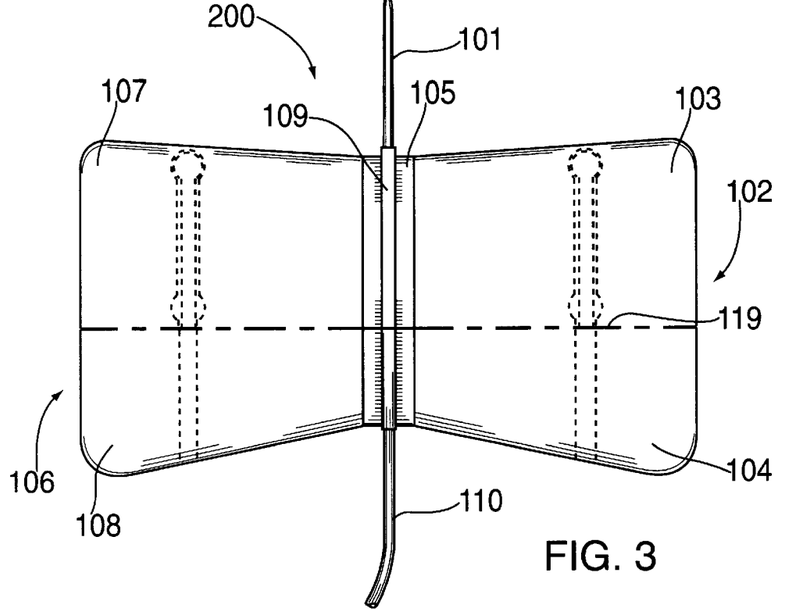
FIG. 3 is a sharps protection system for a blood collection set constructed in accordance with a second preferred embodiment of the invention.
Figure 4:
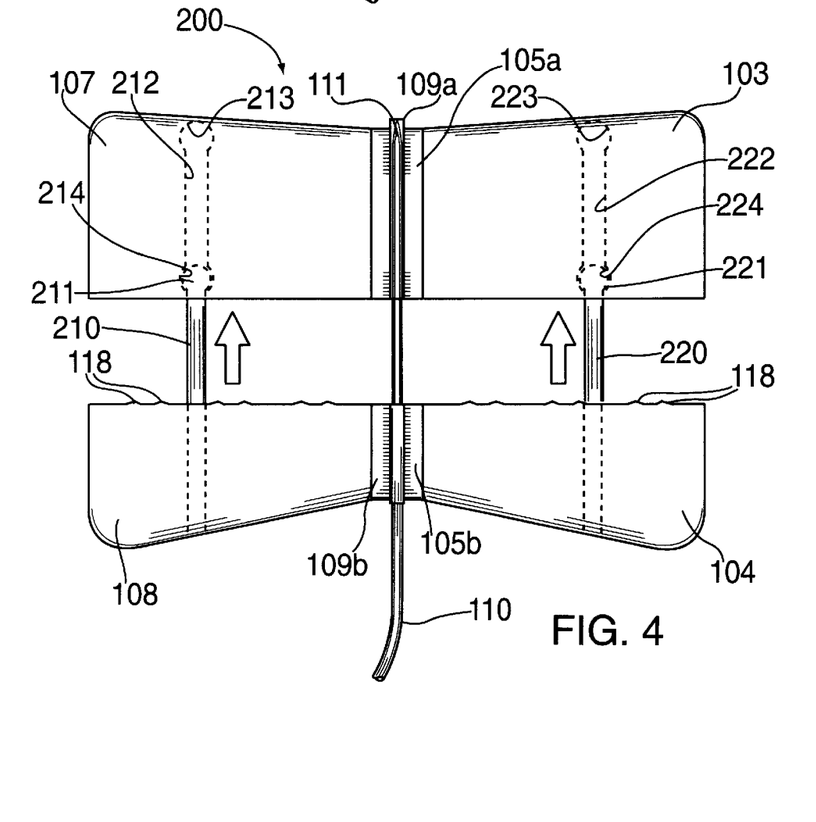
FIG. 4 is a top plan view of the sharps protection system for the blood collection set of FIG. 3 in the post-use sharps protection position.

Reference is next made to FIGS. 3 and 4 wherein a sharps protection system for a blood collection set constructed in accordance with another preferred embodiment of the invention, generally indicated as 200, is depicted, like reference numerals representing like elements. Sharps protection system 200 includes two butterfly wings 102 and 106 as in the embodiment FIG. 1 and has upper and lower portions attached initially across perforation 119. Each of the elements shown in the embodiment of FIGS. 1 and 2 other than the transport mechanism are the same. However, in this case, transport arms 210, 220 include ball and socket arrangements which tend to lock the blood collection set in one of two desired positions. The first position is that shown in FIG. 3 in which the upper and lower portions of the butterfly wings 102, 106 are together and connected by perforation 119. The other is the locked open position shown in FIG. 4 in which balls 211, 221 at the end of transport arms 210, 220 slide into sockets 214, 224 respectively. In operation, balls 213, 223 fit within socket 223, 224 shown in phantom in FIG. 4, when the wings are together in their initial position as shown in FIG. 3. Thereafter, after the perforation 119 is broken and nibs 118 are exposed, the upper portion of butterfly wing 102, 106 (portions 103, 107) move upward along the direction of the arrows in FIG. 4 until balls 211, 221 slide through channels 212 and 213 and are trapped within sockets 214, 224 respectively. This positive locking action prevents needle tip 111 from extending beyond sheath 109a. The positive locking action also provides an audio feedback by clicking as balls 211, 221 slide into sockets 214, 224, respectively.

Figures 5, 6, 7A, 7B:
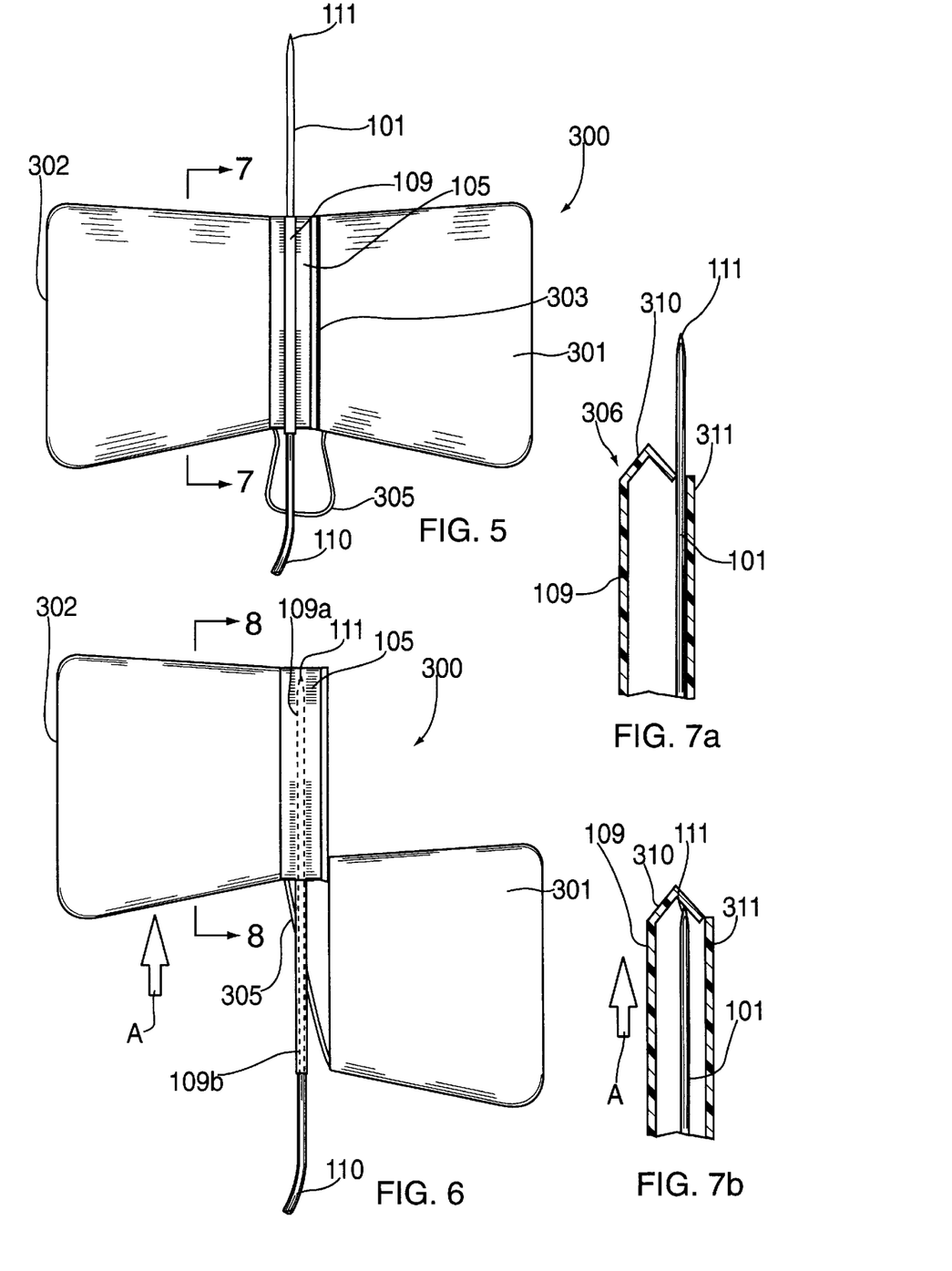
FIG. 5 is a top plan view of a sharps protection system for a blood collection set constructed in accordance with a third preferred embodiment of the invention.
FIG. 6 is a top plan view of the sharps protection system for the blood collection set of FIG. 5 in its post-use sharps protection position.
FIG. 7A is an enlarged partial cross-sectional view of the tip protection component of the sharps protection system of FIGS. 5 and 6 taken along line 7—7 of FIG. 5.
FIG. 7B is a partial cross-sectional view of the tip protection system of FIGS. 5 and 6, following use of the blood collection set taken along line 8—8 of FIG. 6.

Reference is next made to FIGS. 5 and 6 wherein a sharps protection system for a blood collection set constructed in accordance with another preferred embodiment of the invention, generally indicated as 300, is depicted. Like elements are represented by like referenced numerals. The sharps protection system of FIGS. 5 and 6 includes a needle 101 with tip 111 sheath 109 and connector 105. The blood from hollow needle 101 flows out through tubing 110.

The sharp protection system 300 includes butterfly members 301, 302 and a tether 305. In addition, the tip of sheath 109 is shown in cut away views in FIGS. 7a and 7b which relate to the states of FIGS. 5 and 6 respectively.

Following use of blood collection set 300 the health care professional would press upward on wing 302 in the direction of arrow A in FIG. 6. Wing 302 and connector 105 slide upward along wing 301 until wing 302 reaches the position shown in FIG. 6 in which tether 305 is substantially fully extended and tip 111 of needle 101 slides within sheath 109. Tether 305 assures that wing 302 does not separate completely from wing 301. Tether 305 is shown with some play left in it. In various preferred embodiments tether 305 may be taut as soon as sheath 109 extends past tip 111 or may allow varying amounts of limited additional motion beyond tip 111. Tether 305 is, in a preferred embodiment, manufactured of surgical string, plastic, wire or other suitable material which can be maintained sterile. Reference is made to FIGS. 7a and 7b which show locking flap portion 306 which includes hooked cap 310 and sidewall 311. In the position shown in FIG. 5 as well as all positions until tip 111 slides between cap portion 310 and sidewall 311, needle 101 extends out beyond cap 310 and sidewall 311. However, as tip 111 of needle 101 slides between the opening between cap 310 and sidewall 311, needle 101 is trapped within cap 310 so as to prevent needle 111 from sticking out of the top of sheath 109. Cap 310 and sidewall 311 are preferably formed of a springy material which presses against needle 101 and prevents escape by tip 111. Alternately, other trap systems can be used. For example, a flexible sheet can be used which is bent to allow needle tip 111 to extend outward, and then unfolded to block on opening once tip 111 presses it.

Between tether 305, which prevents wing 302 from moving upward along the direction of arrow A beyond the length of tether 305 so that wings 302 and wing 301 remain joined, and tip protection covering 306 including cap section 310 and sidewall 311 of sheath 109, tip 111 is trapped within cap 310 and sidewall 311 and the blood collection set 300 may be disposed of without fear of unwanted contact with tip 111 of needle 101.

Figure 8:
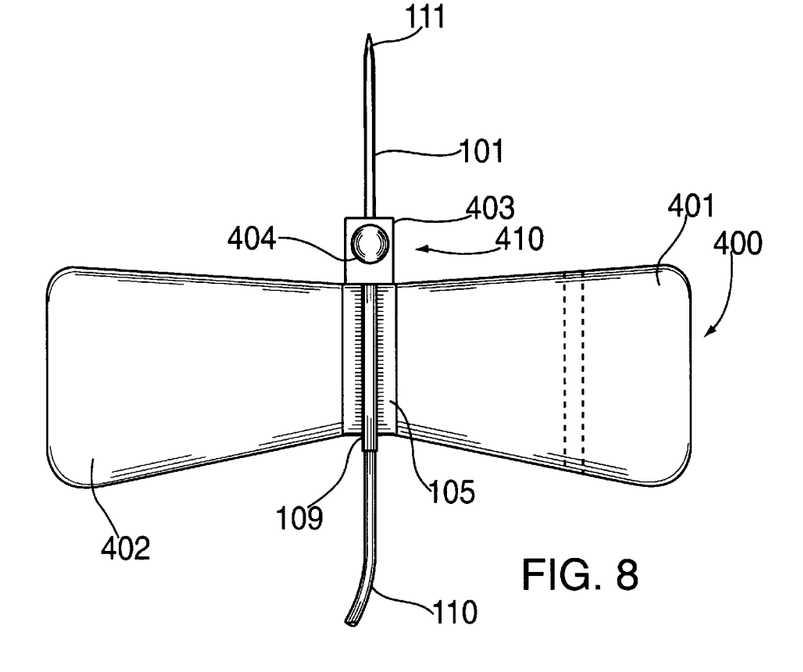
FIG. 8 is a top plan view of a sharps protection system for a blood collection set constructed in accordance with a fourth preferred embodiment of the invention.
Figure 9:
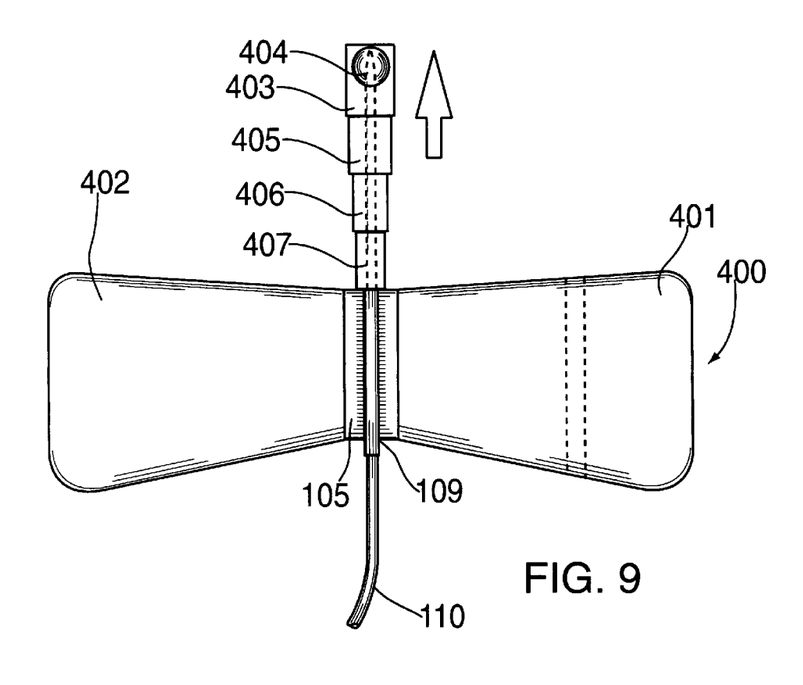
FIG. 9 is a top plan view of the sharps protection system for the blood collection set of FIG. 8 in its post-use sharps protection position.

Reference is next made to FIGS. 8 and 9 wherein a sharps protection system for a blood collection set constructed in accordance with a preferred embodiment of the invention generally referred to as 400 is depicted. Like elements are represented by like reference numerals. In the embodiment of FIG. 400, needle 101 with tip 111 includes wings 401 and 402, a sheath 109 and connector 105. In addition, sharps protection system 400 includes a collapsible protection tube 410. Tube 410 includes an outer section 403 with a finger tip indentation 404, preferably on the upper surface of segment 403.

In operation, once the blood has been drawn from the patient, the health care professional places a thumb or finger into fingertip indentation 404 and presses towards needle tip 111 as the blood collection set and needle 101 are removed from the patient's arm or other body part. As pressure is applied in the direction of tip 111, on fingertip indentation 404, sections 405, 406, 407 (and potentially other sections depending upon the required length of the protection tube), of the tube extend and lock into place. In a preferred embodiment, the opening through which needle 101 and tip 111 extend includes a flap element similar to the structure as shown in FIGS. 7a and 7b so that once tip 111 is trapped within outer segment 403 it cannot easily extend back outward to expose the user to inadvertent contact with tip 111. Collapsible tube 410 in its extended form, as shown in FIG. 9 includes conventional technology which prevents the segments 403, 405, 406, 407 from separating. Likewise, the presence of the needle tip 111 inside segment 403 prevents the collapsible tube 410 from collapsing back to the position shown in FIG. 8. In this way, blood collection set 400 can be easily handled and manipulated without danger of inadvertent contact with needle tip 111. Collapsible tube 410 may be formed either out of a plastic, metal, ceramic or other suitable material which provides suitable protection for needle 101 and tip 111. While collapsible tube 410 is shown with the narrower components closer to butterfly wings 401, 402, an alternate approach in which the wider segments are closer to wings 401, 402 is likewise consistent with applicant's invention.

Figure 10:
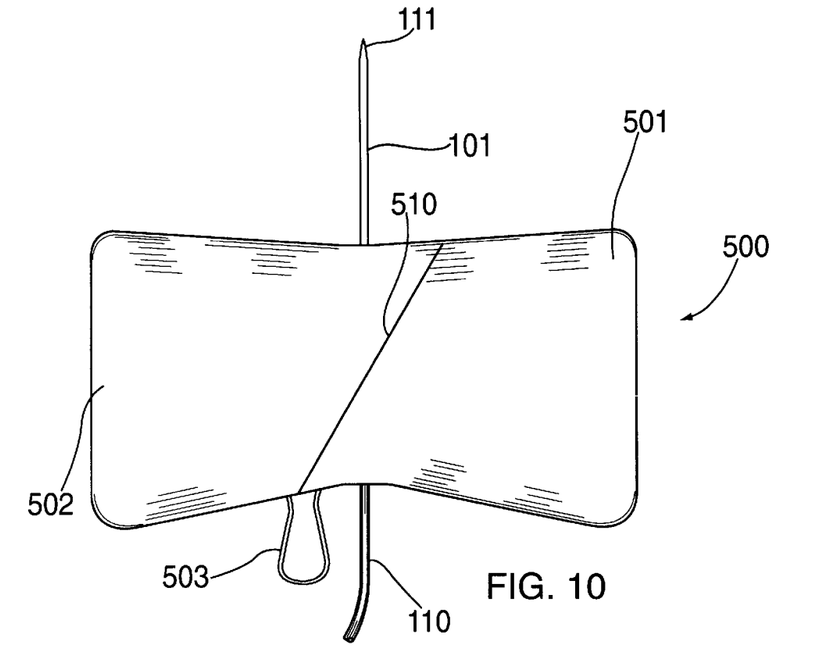
FIG. 10 is a top plan view of a sharps protection system for a blood collection set constructed in accordance with a fifth preferred embodiment of the invention.
Figure 11:
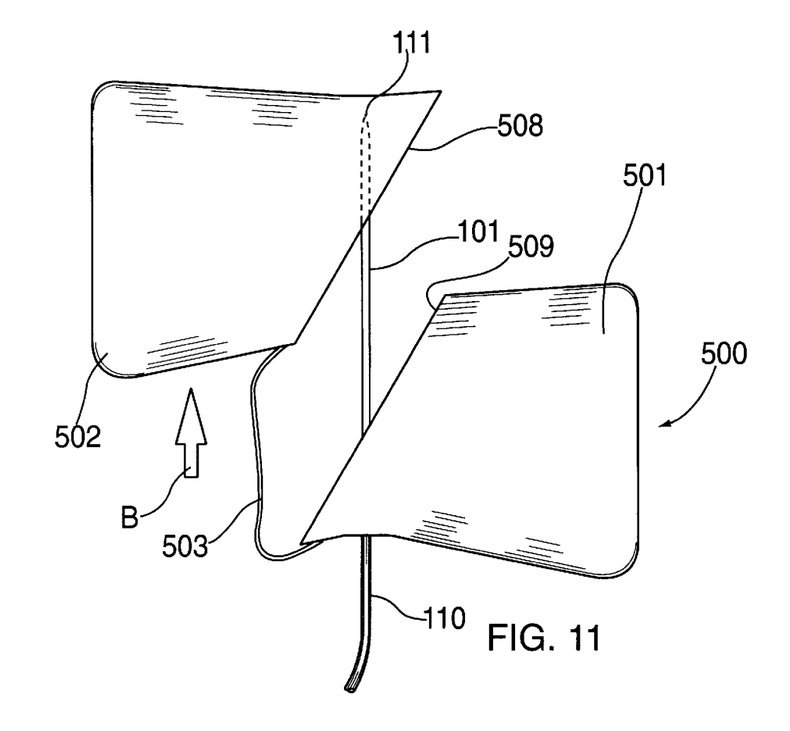
FIG. 11 is a top plan view of the sharps protection system for the blood collection set of FIG. 10 in its post-use sharps protection position.

Reference is next made to FIGS. 10 and 11 in which a sharps protection system for a blood collection set constructed in accordance with another preferred embodiment of the invention is depicted, the sharps protection system being generally indicated as 500. Like elements are represented by like reference numerals. Sharps protection system 500 includes a needle 101 with tip 111 and tubing 110. Butterfly wings 501, 502 are secured along perforation 510 on a diagonal. Sections 501 and 502 are connected by a tether 503. Once the blood collection process has been completed the medical professional presses upwardly on wing 502 in the direction of arrow B (FIG. 11). The two portions 501, 502 separate with section 501 remaining fixed in place. Section 502, which includes a cylindrical groove (not shown) which extends from the top through the edge 508 includes a flapper assembly similar to that shown in FIGS. 7a and 7b, or similar structure which prevents needle tip 111 from extending outwardly once the needle tip 111 slides within wing 502. The flap assembly or other similar structure which allows only a one way movement of needle tip 111 into wing 502, prevents wing 502 from sliding downwardly in a direction opposite to that of arrow B shown in FIG. 11. Similarly, tether 503 prevents wing 502 from sliding off of needle 101 and allowing tip 111 to slide out of wing 502 along surface 508. In this way, needle tip 111 is protected following use and the blood collection set may be safely handled following use and prior to placement in a sharps collection container. The sharps collection system also assures that as the blood collection set is introduced into the sharps collection container no inadvertent contact with needle tip 111 is possible.

Figures 12, 13:
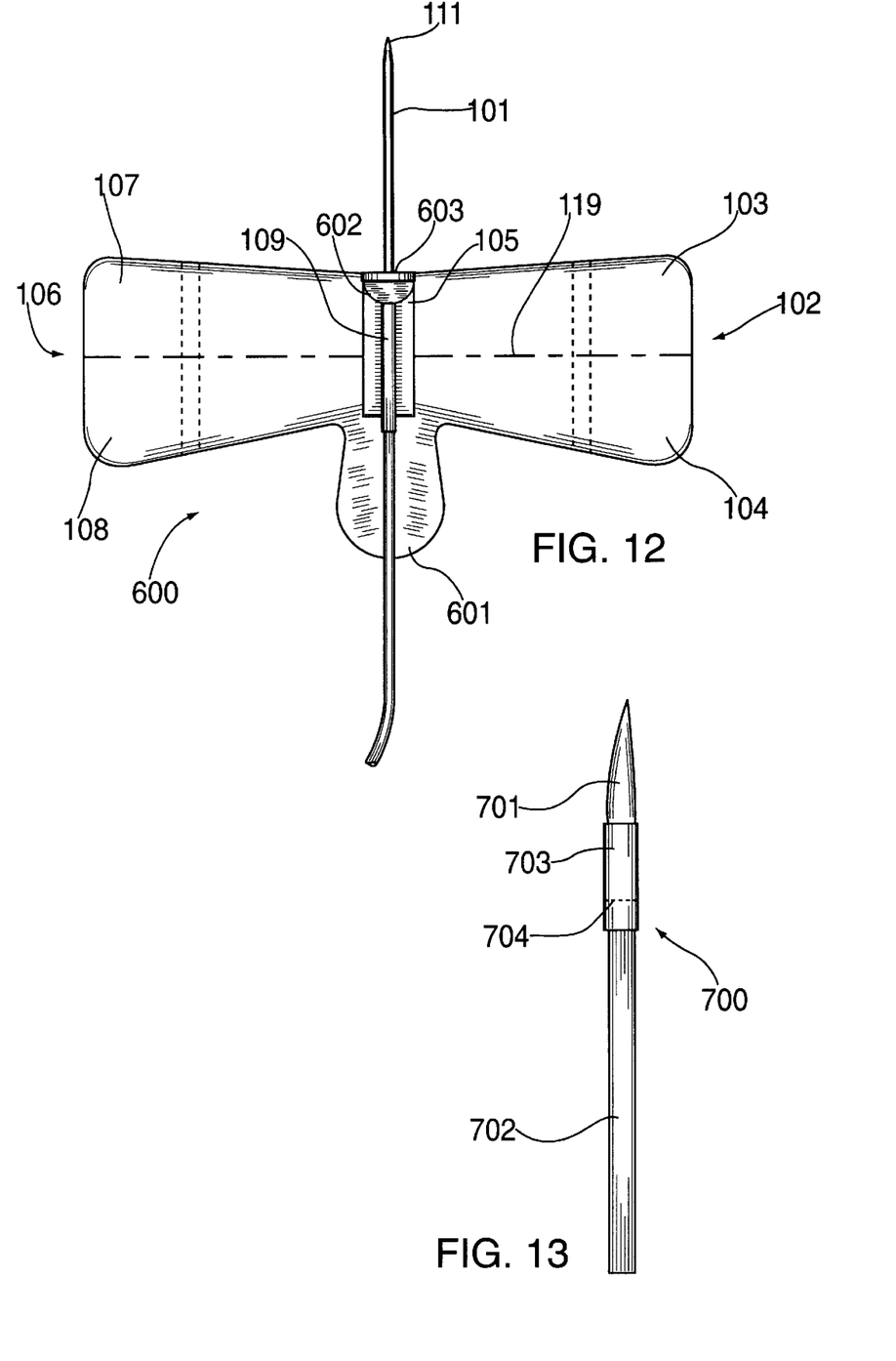
FIG. 12 is a top plan view of a sharps protection system for a blood collection set constructed in accordance with a sixth preferred embodiment of the invention.
FIG. 13 is a top plan view of a sharps protection system for a scalpel constructed in accordance with a seventh preferred embodiment of the invention.

Reference is next made to FIG. 12 wherein a sharps protection system for a blood collection set constructed in accordance with another preferred embodiment of the invention is depicted, the sharps protection system for the blood collection set being generally indicated as 600. Like elements are represented by like referenced numerals. System 600 is substantially identical to the embodiment of FIGS. 1 and 2 except for the addition of a thumb or other finger pad 601 at the base of the butterfly component opposite the needle end of the blood collection set and a second pad 602 at the base of the butterfly component nearer the needle. Base pad 601 provides a stable base to ease the separation of the upper and lower portions of the wings 102 and 106. Second pad 602, with a guard ridge 603, provides a place for a second finger or thumb to allow separation of the parts while protecting the health care professional from inadvertently having a finger slip off the handle and onto needle 101 or tip 111. In operation, with the needle 101 in the patient's arm and blood collection completed, the health care professional would slowly pull downward (in FIG. 12) in the direction away from the needle tip, while retaining the upper portion of the wings in place by applying pressure to second pad 602. This would have effect of insuring that as the needle tip 111 breaks the surface of the patient's skin it would be shielded by sheath 109.

Each of the above embodiments has been directed to a sharps protection system for a blood collection set, and in particular, to a blood collection set incorporating a butterfly type arrangement which enables the medical professional to slide the needle into a patient's arm at a shallow angle. The sharps protection system is equally applicable to other sharps medical implements that are intended to be used once and then safely disposed or discarded. For example, the sharps protection system is suitable for use with any hollow needle and can be used for providing protection for sharps which are used to provide intravenous access, syringes and similar instruments.

Reference is next made to FIG. 13, where a sharps protection system for a scalpel in accordance with another preferred embodiment of the invention, generally indicated as 700, is shown. Sharps protection system 700 includes a scalpel blade 701, which is sharp on one side and the tip handle 702 and guard 703, with perforation 704. Scalpel 700 is used as any normal scalpel. There are several different types of scalpels, with various blade shapes, sizes and thicknesses and varying handles. The sharps protection system in accordance with the invention is appropriate to each of these systems. It is also applicable to scalpels which include a cartridge or disposable blade with a reusable handle. The guard mechanism 703 can be incorporated into the cartridge or disposable blade. In practice, once the scalpel's use is complete, the upper portion of guard 703 (above perforation 704) is pushed upwardly over blade 701 and its tip so that the sharp portions of blade 701 are covered. Various transport mechanisms can be used, including the transport rods, locking chips, tethers and trapping portions which ensure that the upper portion of guard 703 act as a sheath which locks in place over the sharp edge and tip of blade 701. In addition, finger pads and guards, as in FIG. 12, may be used to ease separation of guard 703 and protection for slipping.

With minor modifications the system can be utilized in connection with a reusable sharps instrument, such as a blood collection set. While this is not considered medically desirable in most cases, the embodiment of FIGS. 3 and 4 is particularly suitable for this purpose. With concentrated pressure on the upper portions of the butterfly wings the ball would move out of the socket along the channel to allow the wings to return to their original position shown in FIG. 3. This would require the sockets to be made in a looser fashion so that this reverse movement of the wings would be possible. In a current preferred embodiment the ball and socket arrangement is configured so as to essentially prevent this movement.

An important aspect of the product is the fashion in which a visual indication can be provided to the state of the device. The tubes can be made of colors which will only display a finished colored scheme upon the locking of the wings in a position which assures that the needle tip is covered. Various different ways of utilizing the color as a visual indicator of the state of the sharps protection system are available. One approach is the use of multiple colors which provide for a continuous change in colors until the final position is reached. This could either be the combination or subtraction of colors. Alternatively, a guide rod on which the wings move can be color coded with markings which indicate when the sharps protection system is in its needle tip protecting position. The use of an auditory feedback system where the sharps protection system provides positive feedback as the guard slides into place is also valuable.

It is important to recognize that medicine, particularly in the first world, including the U.S., Western Europe and Japan, have developed an entire method of practice predicated upon the disposability of sharps instruments which pierce a patient's skin or otherwise come in contact with a patient's bodily fluid. This series of procedures has been an outgrowth of the desire to protect both professionals and patients from inadvertent contact with another patient's bodily fluids. As knowledge relating to transmission of the AIDS virus and similar blood and serum based diseases increases, disposable instruments and the need for safety in handling of those disposable instruments (particularly following their intended use in which the instrument comes in contact with a patient's blood or other bodily fluid), careful handling is critical. While sticking oneself with a new medical instrument fresh from a sterile or a separate packaging is painful, it is unlikely to have a negative health effect beyond the pain or discomfort associated with a cut. However, following use of the medical instrument, there is a substantial risk of infection or uncontrolled transmission of bodily fluids. Therefore, it is critical that the instrument be protected from the vagaries of inattentive handling and rough handling after it has been used.

Accordingly, an improved sharps protection system for blood collection sets, syringes, needles, scalpels and other sharp medical instruments by covering the tip of the sharp instrument with an integrally formed or assembled protective covering is provided. The protective covering is in place but does not interfere with the operation of the instrument and prevents the health care professional from inadvertently contacting the sharp tip or blade.

Accordingly, it will thus be seen that the objects set forth above, among those made apparent from the preceding description are efficiently attained and, since certain changes may be made in the above constructions without departing from the spirit and scope of the invention, it is intended that all of the matter contained in the above description or shown in the accompanying drawings, shall be interpreted as illustrative, and not as limiting.

It will also be understood that the following claims are intended to cover all of the generic and specific features of the invention, herein described, and all statements of the scope of the invention which, as a matter of language, might be said to fall there between.

What is claimed is:

1. A sharps protection system, comprising:
   a sharp pointed needle, having a tip at a distal end; and
   a handle, coupled to the needle, proximate the proximal end of the needle, the handle formed as a pair of butterfly wings secured together across the needle, the butterfly wings being separable into a handle portion and a protective portion, the protective portion moving from a first position in which the protective portion and handle portion form the handle to a second position in which the protective portion is separated from the handle portion and covers the tip of the needle.

2. The sharps protective system of claim 1 wherein the handle portion and protective portion separate along a boundary perpendicular to the needle.

3. The sharps protective system of claim 1 wherein the handle portion and protective portion separate along a boundary parallel to the needle.

4. The sharps protective system of claim 1 wherein the handle portion and protective portion separate along a boundary at an acute angle to the needle.

5. The sharps protection system of claim 1 wherein the protection portion moves from the first state to the second state along a guide bar.

6. The sharps protection system of claim 1 further including locking means coupled to the guide bars for locking the protection member in the second state.

7. The sharps protection system of claim 6 wherein the locking means includes a ball and socket system in which a ball proximate an end of one of the guide bars fits into a socket in the protective member or handle member.

8. The sharps protection system of claim 6 wherein the locking means includes tabs secured to the guide bars for preventing the protective portion from moving along the guide bar from the second state.

9. The sharps protection system of claim 1 further including a connector for restricting movement of the protective member from the handle member by more than a predetermined distance.

10. The sharps protection system of claim 1 wherein the handle portion and protective portion are connected along a perforated boundary.

11. The sharps protection system of claim 1 wherein the needle is hollow and the sharps protection system further includes a liquid passage member secured to the proximal end of the needle for receiving bodily fluids passing from the needle tip through the needle.

12. The sharps protection system of claim 1 wherein the protective portion includes a flapper assembly which covers the tip of the needle when the protective portion is in the second position.

13. The sharps protection system of claim 9 wherein the connector is a string member having a length established to allow the protective portion to cover the tip of the needle and prevent the protective portion from sliding off the needle.

14. The sharps protection system of claim 13 further including a locking mechanism for preventing the protective portion from moving from the second position back to the first position.

15. The sharps protection system of claim 14 wherein the locking mechanism includes a flapper arrangement which rests against the tip of the needle.

16. The sharps protection system of claim 14 wherein the protection portion moves from the first state to the second state along a guide bar and the locking mechanism engages with the guide bars.

17. The sharps protection system of claim 16 wherein the locking mechanism includes a ball and socket system in which a ball proximate an end of a guide bar fits into a socket in the protective member or handle member.

18. The sharps protection system of claim 16 wherein the locking mechanism includes tabs secured to a guide bar.

19. A sharps protection system, comprising:
   a sharp pointed needle, having a tip at a distal end; and
   a handle, coupled to the needle, proximate the proximal end of the needle, the handle formed as a pair of butterfly wings secured together across the needle, the butterfly wings being separable into a handle portion and a protective portion along a boundary running perpendicular to the needle, the protective portion moving from a first position in which the protective portion and handle portion form the handle to a second position in which the protective portion is separated from the handle portion and covers the tip of the needle.

20. The sharps protection system of claim 19 wherein the protection portion moves from the first state to the second state along a guide bar.

21. The sharps protection system of claim 19 further including locking means coupled to the guide bars for locking the protection member in the second state.

22. The sharps protection system of claim 21 wherein the locking means includes a ball and socket system in which a ball proximate an end of one of the guide bars fits into a socket in the protective member or handle member.

23. The sharps protection system of claim 21 wherein the locking means includes tabs secured to the guide bars for preventing the protective portion from moving along the guide bar from the second state.

24. The sharps protection system of claim 19 further including a connector for restricting movement of the protective member from the handle member by more than a predetermined distance.

25. The sharps protection system of claim 19 wherein the handle portion and protective portion are connected along a perforated boundary.

26. The sharps protection system of claim 19 wherein the needle is hollow and the sharps protection system further includes a liquid passage member secured to the proximal end of the needle for receiving bodily fluids passing from the needle tip through the needle.

27. The sharps protection system of claim 19 wherein the protective portion includes a flapper assembly which covers the tip of the needle when the protective portion is in the second position.

28. The sharps protection system of claim 24 wherein the connector is a string member having a length established to allow the protective portion to cover the tip of the needle and prevent the protective portion from sliding off the needle.

29. The sharps protection system of claim 24 further including a locking mechanism for preventing the protective portion from moving from the second position back to the first position.

30. The sharps protection system of claim 29 wherein the locking mechanism includes a flapper arrangement which rests against the tip of the needle.

31. The sharps protection system of claim 29 wherein the protection portion moves from the first state to the second state along a guide bar and the locking mechanism engages with the guide bars.

32. The sharps protection system of claim 31 wherein the locking mechanism includes a ball and socket system in which a ball proximate an end of a guide bar fits into a socket in the protective member or handle member.

33. The sharps protection system of claim 31 wherein the locking mechanism includes tabs secured to a guide bar.

34. A sharps protection system, comprising:
   a sharp pointed needle, having a tip at a distal end; and
   a handle, coupled to the needle, proximate the proximal end of the needle, the handle formed as a pair of butterfly wings secured together across the needle, the butterfly wings being separable into a handle portion and a protective portion along a boundary running parallel to the needle, the protective portion moving from a first position in which the protective portion and handle portion form the handle to a second position in which the protective portion is separated from the handle portion and covers the tip of the needle.

35. The sharps protection system of claim 34 wherein the protection portion moves from the first state to the second state along a guide bar.

36. The sharps protection system of claim 34 further including locking means coupled to the guide bars for locking the protection member in the second state.

37. The sharps protection system of claim 36 wherein the locking means includes a ball and socket system in which a ball proximate an end of one of the guide bars fits into a socket in the protective member or handle member.

38. The sharps protection system of claim 36 wherein the locking means includes tabs secured to the guide bars for preventing the protective portion from moving along the guide bar from the second state.

39. The sharps protection system of claim 34 further including a connector for restricting movement of the protective member from the handle member by more than a predetermined distance.

40. The sharps protection system of claim 34 wherein the handle portion and protective portion are connected along a perforated boundary.

41. The sharps protection system of claim 34 wherein the needle is hollow and the sharps protection system further includes a liquid passage member secured to the proximal end of the needle for receiving bodily fluids passing from the needle tip through the needle.

42. The sharps protection system of claim 34 wherein the protective portion includes a flapper assembly which covers the tip of the needle when the protective portion is in the second position.

43. The sharps protection system of claim 39 wherein the connector is a string member having a length established to allow the protective portion to cover the tip of the needle and prevent the protective portion from sliding off the needle.

44. The sharps protection system of claim 43 further including a locking mechanism for preventing the protective portion from moving from the second position back to the first position.

45. The sharps protection system of claim 44 wherein the locking mechanism includes a flapper arrangement which rests against the tip of the needle.

46. The sharps protection system of claim 44 wherein the protection portion moves from the first state to the second state along a guide bar and the locking mechanism engages with the guide bars.

47. The sharps protection system of claim 46 wherein the locking mechanism includes a ball and socket system in which a ball proximate an end of a guide bar fits into a socket in the protective member or handle member.

48. The sharps protection system of claim 46 wherein the locking mechanism includes tabs secured to a guide bar.

49. A sharps protection system, comprising:
   a sharp pointed needle, having a tip at a distal end; and
   a handle, coupled to the needle, proximate the proximal end of the needle, the handle formed as a pair of butterfly wings secured together across the needle, the butterfly wings being separable into a handle portion and a protective portion along a boundary running at an acute angle to the needle, the protective portion moving from a first position in which the protective portion and handle portion form the handle to a second position in which the protective portion is separated from the handle portion and covers the tip of the needle.

50. The sharps protection system of claim 49 wherein the protection portion moves from the first state to the second state along a guide bar.

51. The sharps protection system of claim 49 further including locking means coupled to the guide bars for locking the protection member in the second state.

52. The sharps protection system of claim 51 wherein the locking means includes a ball and socket system in which a ball proximate an end of one of the guide bars fits into a socket in the protective member or handle member.

53. The sharps protection system of claim 51 wherein the locking means includes tabs secured to the guide bars for preventing the protective portion from moving along the guide bar from the second state.

54. The sharps protection system of claim 49 further including a connector for restricting movement of the protective member from the handle member by more than a predetermined distance.

55. The sharps protection system of claim 49 wherein the handle portion and protective portion are connected along a perforated boundary.

56. The sharps protection system of claim 49 wherein the needle is hollow and the sharps protection system further includes a liquid passage member secured to the proximal end of the needle for receiving bodily fluids passing from the needle tip through the needle.

57. The sharps protection system of claim 49 wherein the protective portion includes a flapper assembly which covers the tip of the needle when the protective portion is in the second position.

58. The sharps protection system of claim 54 wherein the connector is a string member having a length established to allow the protective portion to cover the tip of the needle and prevent the protective portion from sliding off the needle.

59. The sharps protection system of claim 58 further including a locking mechanism for preventing the protective portion from moving from the second position back to the first position.

60. The sharps protection system of claim 59 wherein the locking mechanism includes a flapper arrangement which rests against the tip of the needle.

61. The sharps protection system of claim 59 wherein the protection portion moves from the first state to the second state along a guide bar and the locking mechanism engages with the guide bars.

62. The sharps protection system of claim 61 wherein the locking mechanism includes a ball and socket system in which a ball proximate an end of a guide bar fits into a socket in the protective member or handle member.

63. The sharps protection system of claim 61 wherein the locking mechanism includes tabs secured to a guide bar.

* * * * *